United States Patent
Hill et al.

(10) Patent No.: US 10,814,111 B2
(45) Date of Patent: Oct. 27, 2020

(54) SURGICAL DRAIN LINE STRIPPING DEVICES

(71) Applicant: Mayo Foundation for Medical Education and Research, Rochester, MN (US)

(72) Inventors: Robert B. Hill, Rochester, MN (US); Michael J. Thorn, Jr., Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 303 days.

(21) Appl. No.: 15/729,163

(22) Filed: Oct. 10, 2017

(65) Prior Publication Data

US 2018/0099127 A1    Apr. 12, 2018

Related U.S. Application Data

(60) Provisional application No. 62/406,609, filed on Oct. 11, 2016.

(51) Int. Cl.
*A61M 1/00* (2006.01)
*A61M 27/00* (2006.01)
*A61B 90/70* (2016.01)

(52) U.S. Cl.
CPC ............. *A61M 27/00* (2013.01); *A61B 90/70* (2016.02); *A61M 1/0078* (2013.01); *A61B 2090/701* (2016.02); *A61M 2209/10* (2013.01)

(58) Field of Classification Search
CPC ............. A61M 27/00; A61M 2209/10; A61M 1/0078; A61B 90/70; A61B 2090/701; A61B 17/0008
See application file for complete search history.

(56) References Cited

U.S. PATENT DOCUMENTS

| | | | | |
|---|---|---|---|---|
| 5,318,546 A | * | 6/1994 | Bierman | A61M 39/284 128/898 |
| 7,309,055 B1 | * | 12/2007 | Spiegel | A61M 1/0078 222/102 |
| 7,998,168 B2 | | 8/2011 | Kleimann | |
| 2004/0267305 A1 | | 12/2004 | Borgman | |
| 2016/0294168 A1 | * | 10/2016 | Hoppe | B25B 7/02 |

* cited by examiner

*Primary Examiner* — Peter S Vasat
*Assistant Examiner* — Meagan Ngo
(74) *Attorney, Agent, or Firm* — Fish & Richardson P.C.

(57) ABSTRACT

Medical drain lines tend to become clogged with blood or pus and thereafter lose their efficacy. Devices can be used for stripping blockages from medical drainage lines. For example, this document describes various devices that can be manually operated to progressively compress (along the length of the drain line) a surgical drain line to forcibly strip out blockages from within the drain line.

8 Claims, 3 Drawing Sheets

SURGICAL DRAIN LINE STRIPPING DEVICES

CROSS-REFERENCE TO RELATED APPLICATIONS

This application claims benefit of priority from U.S. Provisional Application Ser. No. 62/406,609, filed on Oct. 11, 2016.

BACKGROUND

1. Technical Field

This document relates to devices for stripping blockages from medical drainage lines and methods for their use. For example, this document relates to devices that can be manually operated to progressively compress (along the length of the drain line) a surgical drain line to forcibly strip out blockages from within the drain line.

2. Background Information

Medical drainage lines are clear or opaque plastic tubes that are used to remove blood, pus and other bodily fluids from a patient's wound (e.g., surgical space, cavity, abscess). Depending on the location of the drainage line and the volume of the effluent, the drain line may remain in place for days to weeks or longer.

Drainage lines may be connected to a drainage reservoir such as a wall suction device, portable suction device, or may be left to drain naturally by gravity. One of the most common types of drainage lines used is a Jackson Pratt (JP) drain. The JP drain consists of a plastic drainage tube that is connected to one of the aforementioned drainage reservoirs used to remove bodily fluids from a patient's wound. The drainage line only functions as intended if there is no occlusion or blockage in the drainage line between the patient's wound and drainage reservoir.

Drainage lines have a tendency to become clogged causing a loss of patency. Drainage lines require routine cares including, but not limited to, routine stripping or milking of the drainage line to ensure proper drain function. If the drainage line becomes clogged, bodily fluids could accumulate within the patient's surgical wound, which can lead to complications. For example, the accumulation of fluids may put increased pressure on adjacent organs, delay healing, increase pain, or become a nidus for infection. Once a drainage line becomes clogged, the drainage line is sometimes removed or may need to be exchanged under X-ray guidance or replaced surgically, as it no longer providing the intended benefit.

SUMMARY

This document describes devices for stripping blockages from medical drainage lines and methods for their use. For example, this document describes devices that can be manually operated to progressively compress (along the length of the drain line) a surgical drain line to forcibly strip out blockages from within the drain line.

In one implementation, a device for stripping a medical line includes a first portion defining one or more channels and a second portion pivotably coupled to the first portion whereby the device can be arranged in a closed configuration and one or more open configurations. The second portion defines one or more channels. While the device is arranged in the closed configuration, at least one channel of the first portion is positioned adjacent and parallel to at least one channel of the second portion to define at least one passage configured for receiving the medical line.

Such a device may optionally include one or more of the following features. The at least one passage may be round at a first end of the passage and may be a slot at a second end of the passage. The at least one passage may be tapered. The first portion may be hinged to the second portion about a hinge axis. The hinge axis may be parallel with the passage. The first portion may be separated from the second portion while the device is arranged in a fully open configuration. The first portion may be detained in contact with the second portion while the device is arranged in the closed configuration. The first portion and the second portion may each define at least two channels. While the device is arranged in the closed configuration, at least two channels of the first portion may be positioned adjacent and parallel to at least two channels of the second portion to define at least two passages configured for receiving the medical line. The at least two passages may be round at a first end of the passages and may be a slot at a second end of the passages. The at least two passages may be of differing dimensions.

In another aspect, this disclosure is directed to a method for stripping a medical line of blockage material within the medical line. The method includes: placing the medical line in a first channel defined by a first portion of a line stripping device; closing the line stripping device onto the medical line by pivoting a second portion of the line stripping device toward the first portion, wherein a second channel defined by the second portion of the line stripping device receives the medical line; compressing the medical line between the first and second portions of the line stripping device while the medical line is in the first channel and the second channel; and while compressing the medical line between the first and second portions of the line stripping device, pulling the line stripping device along the medical line.

Such a method may optionally include one or more of the following features. The first channel and the second channel may together form a tapered passage. The tapered passage, along with the compressing and the pulling, may progressively compresses the medical line to move the blockage material within the medical line. The first channel and the second channel may together define a passage that is round at a first end of the passage and that is a slot at a second end of the passage. The pulling may be performed with the first end of the passage arranged as a leading end of the passage and the second end of the passage arranged as a trailing end of the passage in relation to the medical line.

Particular embodiments of the subject matter described in this document can be implemented to realize one or more of the following advantages. Currently, stripping of drainage lines is performed by firmly pinching or compressing the drainage tubing between two fingers and sliding the fingers the length of the tubing from where the tubing exits the body towards the drainage reservoir. Sometimes a damp cloth, alcohol pad, or other sort of lubricating substance is used to make the stripping process easier. Stripping is also sometimes accomplished by compressing the tubing on the side of a pen or pair of scissors and running the length of the tubing like curling a ribbon when gift wrapping. Drain line stripping in these manners can be difficult to perform, especially for people with strength or dexterity issues. In contrast, the devices provided herein can provide a shapely gripping-surface and greater leverage for enhanced ease-of-use and efficacy in comparison to conventional drain stripping techniques. In result, patients may experience faster healing and less risk of complications after surgery. The stripping devices provided herein are also advantageously designed to be easily disassembled for cleaning and maintenance. Hence, the stripping devices are designed to be reused multiple times.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices for stripping blockages from medical drainage lines and methods for their use. For example, this document describes devices that can be manually operated to progressively compress (by sliding the device along the length of the drain line) a surgical drain line to forcibly strip out blockages from within the drain line.

Figure 1:
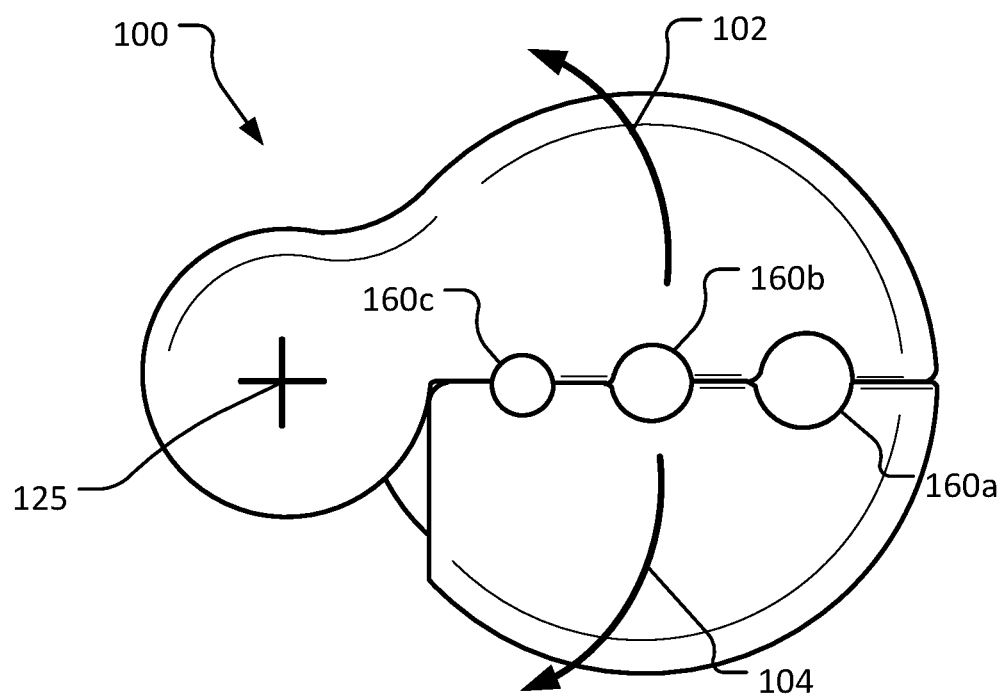
FIG. 1 is a front view of a first example drain line stripping device in accordance with some embodiments provided herein.
Figure 2:
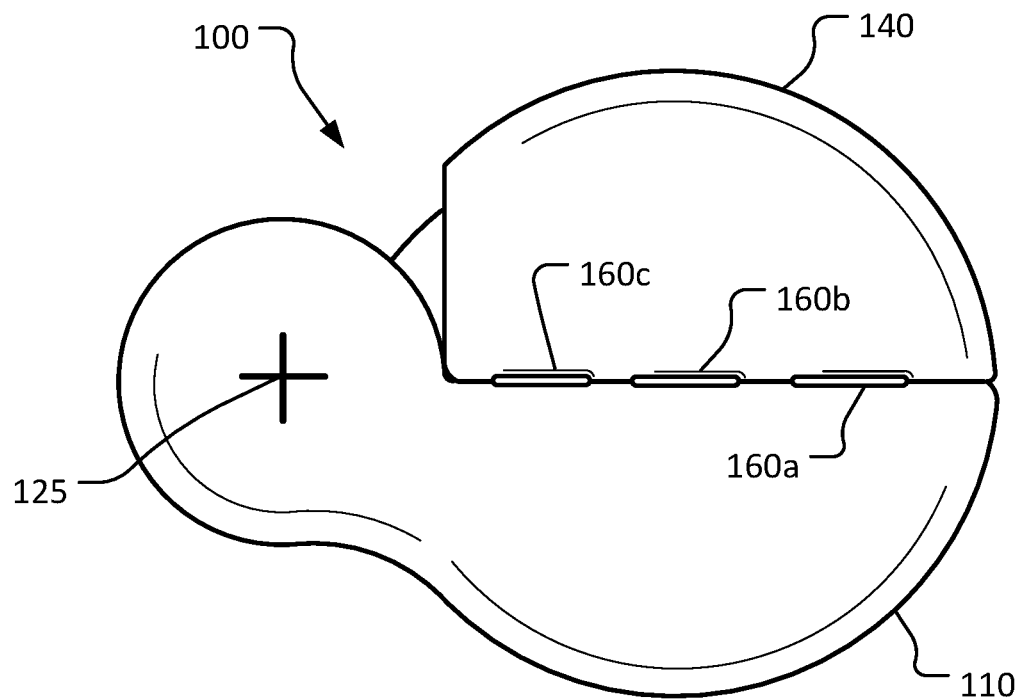
FIG. 2 is a back view of the drain line stripping device of FIG. 1.

Referring to FIGS. 1 and 2, an example drain stripping device 100 can be used to progressively compress (by sliding device 100 along the length of a drain line) a surgical drain line to forcibly strip out blockages from within the drain line. FIG. 1 is a front view of device 100, and FIG. 2 is a back view of the 100. In both FIG. 1 and FIG. 2, the drain stripping device 100 is depicted in its closed configuration.

Drain stripping device 100 includes a first portion 110 and a second portion 140. First portion 110 and second portion 140 are pivotably coupled to each other. In particular, first portion 110 and second portion 140 are pivotably coupled at a hinge with an axis 125. For simplicity, it can be said that first portion 110 and second portion 140 are pivotably coupled about hinge 125. As first portion 110 and second portion 140 are pivoted to open the drain stripping device 100, first portion 110 follows an arcuate path depicted by arrow 102 and second portion 140 follows an arcuate path depicted by arrow 104. Hence, it can be said that drain stripping device 100 has a clam shell configuration (because first portion 110 and second portion 140 can pivot between the open and closed configurations like a clam shell).

While first portion 110 and second portion 140 are in the closed configuration as depicted, the interface between portions 110 and 140 define three tapered passages 160a, 160b, and 160c. Tapered passages 160a, 160b, and 160c are configured to receive drain lines of differing sizes. Drain stripping device 100 can be configured to accommodate drain lines of all sizes.

It can be seen that the front ends (FIG. 1) of tapered passages 160a, 160b, and 160c are circular openings, and the back ends (FIG. 2) of tapered passages 160a, 160b, and 160c are flat slots. The tapered passages 160a, 160b, and 160c gradually transition from being round at the front end to being flat at the back end. That is, along the thickness of drain stripping device 100, tapered passages 160a, 160b, and 160c become gradually flatter (more ovular) from the front circular shapes to the back slot shapes.

Tapered passages 160a, 160b, and 160c are comprised by channels defined in first portion 110 and second portion 140. In some embodiments, the channels can be mirror images of each other. When the channels are brought adjacent to each other, tapered passages 160a, 160b, and 160c through drain stripping device 100 are created.

While the depicted drain stripping device 100 includes three tapered passages 160a, 160b, and 160c, in some embodiments one, two, four, five, six, seven, or more than seven tapered passages are defined in a single drain stripping device 100.

The materials of construction of drain stripping device 100 can be various polymeric or metallic materials. For example, in some embodiments drain stripping device 100 can be made of polymeric materials such as, but not limited to, polystyrene (PS), acrylonitrile butadiene styrene (ABS), polyvinyl chloride (PVC), modified polyethylene terephthalate glycol (PETG), cellulose acetate butyrate (CAB), polyethylene (PE), high density polyethylene (HDPE), low density polyethylene (LDPE or LLDPE), polypropylene (PP), polymethylpentene (PMP), polycarbonate (PC), polyphenylene oxide (PPO), modified polyphenylene oxide (Mod PPO), polyphenelyne ether (PPE), modified polyphenelyne ether (Mod PPE), thermoplastic polyurethane (TPU), polyamide (PA or Nylon), polyoxymethylene (POM or Acetal), polyethylene terephthalate (PET, Thermoplastic Polyester), polybutylene terephthalate (PBT, Thermoplastic Polyester), ultra high molecular weight polyethylene (UHMW-PE), and the like. In some embodiments, drain stripping device 100 can be made of metallic materials such as, but not limited to, aluminum, aluminum alloys, stainless steel, stainless steel alloys, and the like.

To use drain stripping device 100, the user will first pivot drain stripping device 100 open and place it around the drain line. The user will select an appropriate one of tapered passages 160a, 160b, or 160c in accordance with the size of the drain line. Then the user will close drain stripping device 100 onto the drain line with the drain line located in the selected one of the tapered passages 160a, 160b, or 160c. The front of drain stripping device 100 (as shown in FIG. 1) will be facing away from the patient, and the back of drain stripping device 100 (as shown in FIG. 2) will be facing towards the patient. Then, while compressing drain stripping device 100 in the closed configuration around the drain line, the user will slide drain stripping device 100 along the drain line in a direction away from the patient. As the user slides drain stripping device 100 along the drain line, occluding materials (e.g., pus or blood) within the drain line will be forced along the drain line. The user will continue sliding drain stripping device 100 all the way to the end of the drain line, and off of the drain line. As drain stripping device 100 is pulled off of the end of the drain line, the occluding materials will be forced out of the drain line. In this manner, drain stripping device 100 will strip a drain line of occluding materials.

In some embodiments, drain stripping device 100 can be disassembled for cleaning. For example, in some embodiments first portion 110 and second portion 140 can become uncoupled from each other by pivoting them to the fully open configuration. Cleaning can be performed using an alcohol wipe, autoclaving, immersion in soap and water, and any other suitable technique, and combinations thereof.

Figure 3:
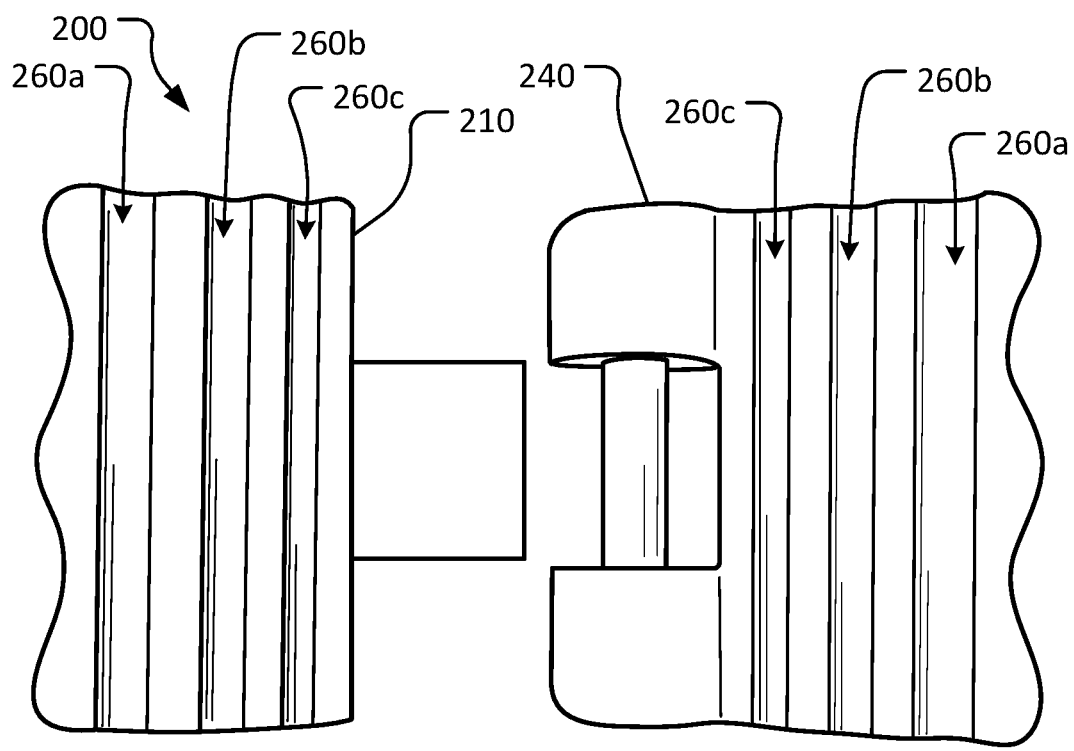
FIG. 3 is an internal view of another example drain line stripping device in accordance with some embodiments provided herein. The drain line stripping device is shown in a disassembled configuration.
Figure 4:
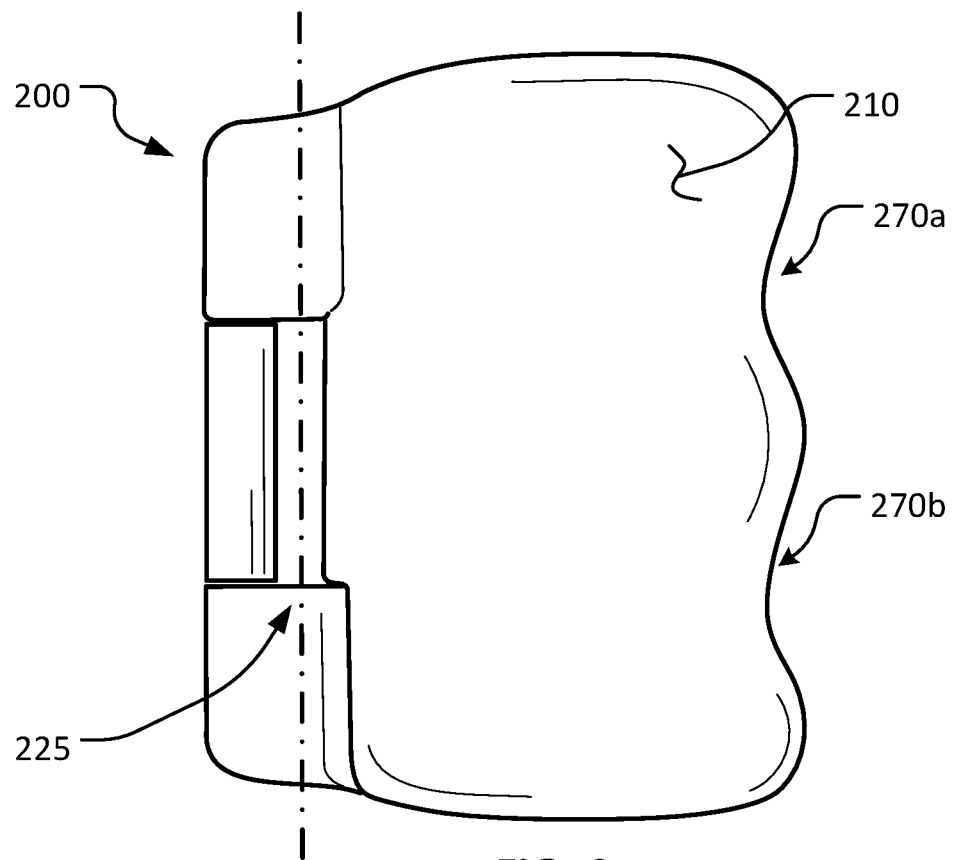
FIG. 4 is a top view of the drain line stripping device of FIG. 3 in an assembled and closed configuration.
Figure 5:
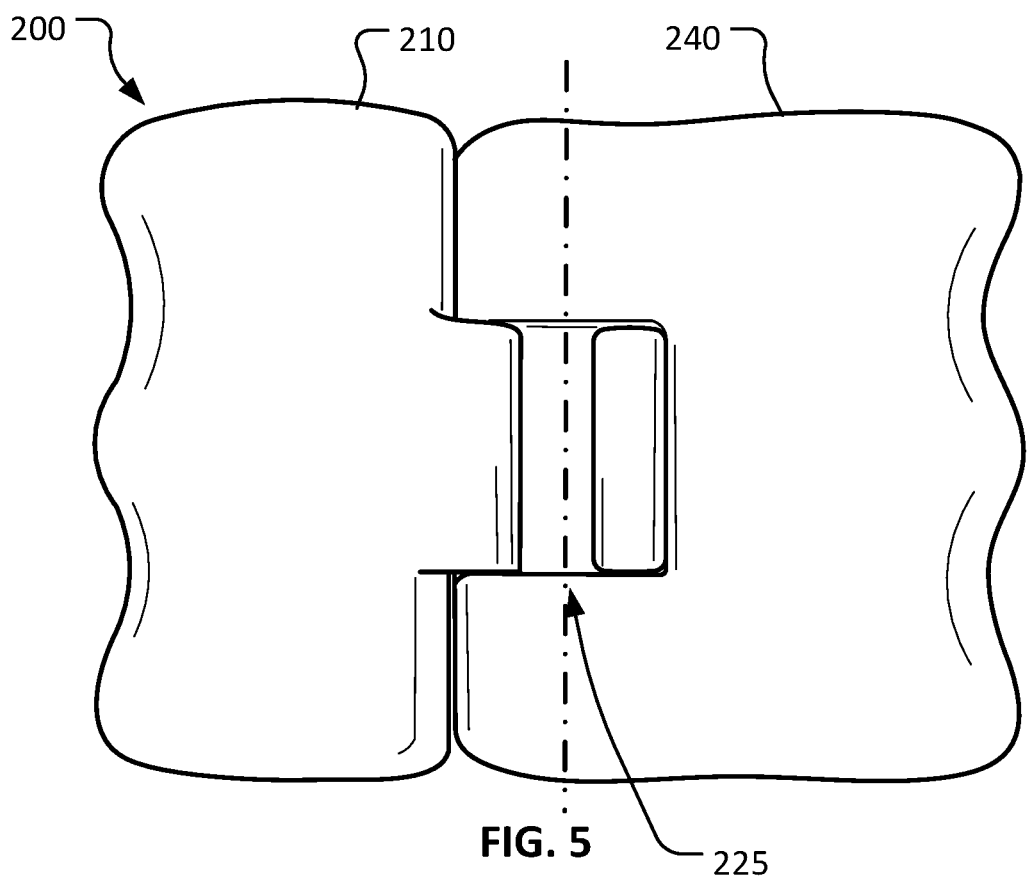
FIG. 5 is a top view of the drain line stripping device of FIG. 3 in an assembled and open configuration.
Figure 6:
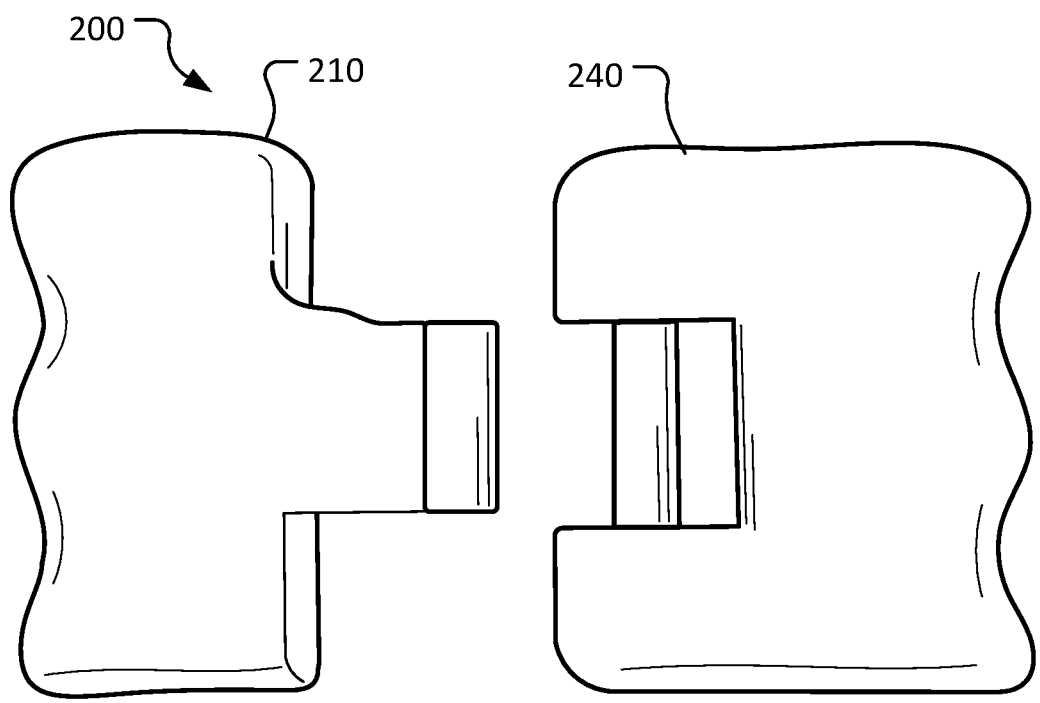
FIG. 6 is top view of the drain line stripping device of FIG. 3 in a disassembled configuration.

Referring to FIGS. 3-6, another example drain stripping device 200 can be used to progressively compress (by sliding device 200 along the length of a drain line) a surgical drain line to forcibly strip out blockages from within the drain line. FIG. 3 is an open and disassembled view showing the internal tapered passages of drain stripping device 200. FIG. 4 is a closed view of drain stripping device 200. FIG. 5 is an open assembled view showing the outside of drain stripping device 200. FIG. 6 is an open disassembled view showing the outside of drain stripping device 200.

Drain stripping device 200 can be made from the same types of materials that are described above in reference to drain stripping device 100. Drain stripping device 200 can be used in the same manner as described above in reference to drain stripping device 100.

In the depicted embodiment, drain stripping device 200 includes a first portion 210 and a second portion 240. First portion 210 and second portion 240 are pivotably coupled to each other. In particular, first portion 210 and second portion 240 are pivotably coupled at a hinge with an axis 225. For simplicity, it can said that first portion 210 and second portion 240 are pivotably coupled about hinge 225. Hence, it can be said that drain stripping device 200 has a clam shell configuration (because first portion 210 and second portion 240 can pivot between the open and closed configurations like a clam shell).

While first portion 210 and second portion 240 are in the closed configuration as depicted, the interface between portions 210 and 240 define three tapered passages 260*a*, 260*b*, and 260*c*. Tapered passages 260*a*, 260*b*, and 260*c* are configured to receive drain lines of differing sizes. Drain stripping device 200 can be configured to accommodate drain lines of all sizes.

In some embodiments, the front or leading ends of tapered passages 260*a*, 260*b*, and 260*c* are circular openings, and the back or trailing ends (FIG. 2) of tapered passages 260*a*, 260*b*, and 260*c* are flat slots. The tapered passages 260*a*, 260*b*, and 260*c* gradually transition from being round at the front end to being flat at the back end. That is, along the thickness of drain stripping device 200, tapered passages 260*a*, 260*b*, and 260*c* become gradually flatter from the front circular shapes to the back slot shapes.

As best seen in FIG. 3, tapered passages 260*a*, 260*b*, and 260*c* are formed by channels that are defined within first portion 210 and second portion 240. While drain stripping device 200 is arranged in the closed configuration, the channels of first portion 210 are positioned adjacent and parallel to the channels of second portion 240 to define tapered passages 260*a*, 260*b*, and 260*c* configured for receiving a medical drain line.

While the depicted drain stripping device 200 includes three tapered passages 260*a*, 260*b*, and 260*c*, in some embodiments one, two, four, five, six, seven, or more than seven tapered passages are defined in a single drain stripping device 200.

Drain stripping device 200 can be readily disassembled for cleaning. To disassemble drain stripping device 200, hinge 225 can be uncoupled by first pivoting first portion 210 and second portion 240 wide open in relation to each other (e.g., as shown in FIGS. 3 and 5) and then hinge 225 can be easily separated (as shown in FIG. 6). The ease of disassembly facilitates cleaning of drain stripping device 200.

In the depicted embodiment, the outer surface of drain stripping device 200 includes contours that allow for strong grasping or gripping of drain stripping device 200 by a user. For example, first portion 210 and second portion 240 include contours 270*a* and 270*b*. Contours 270*a* and 270*b* may receive the user's fingers, for example.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for stripping a first and a second sized medical line, the device comprising:
   a first portion; and
   a second portion pivotably coupled to the first portion whereby the device can be arranged in a closed configuration and one or more open configurations,
   wherein the first portion defines at least a first channel and a third channel, wherein the second portion defines at least a second channel and a fourth channel, wherein, while the device is arranged in the closed configuration the first channel of the first portion is positioned adjacent and parallel to the second channel of the second portion to define a first passage configured for receiving the first sized medical line, wherein, while the device is arranged in the closed configuration, the third channel of the first portion is positioned adjacent and parallel to the fourth channel of the second portion to define a second passage configured for receiving the second sized medical line, wherein a first end opening of the first passage is a circular opening and a second end opening of the first passage is a flat slot;

wherein the first passage defines a first passage axis extending from the first end opening of the first passage to the second end opening of the first passage, wherein the first passage has a cross-sectional shape normal to the first passage axis, wherein the cross-sectional shape of the first passage gradually transitions along the first passage between the circular opening at the first end opening of the first passage and the flat slot at the second end opening of the first passage, wherein a first end opening of the second passage is a circular opening, wherein a second end opening of the second passage is a flat slot, wherein the second passage defines a second passage axis extending from the first end opening of the second passage to the second end opening of the second passage, wherein the second passage has a cross-sectional shape normal to the second passage axis, wherein the cross-sectional shape of the second passage gradually transitions along the second passage between the circular opening at the first end opening of the second passage and the flat slot at the second end opening of the second passage, wherein the circular opening of the first passage is of a differing dimension from the circular opening of the second passage, wherein the flat slot of the first passage is of a differing dimension from the flat slot of the second passage, wherein the first portion is hinged to the second portion about a hinge axis, and wherein the hinge axis is parallel with the first passage axis.

2. The device of claim 1, wherein the first passage is tapered.

3. The device of claim 1, wherein the first portion can be separated from the second portion while the device is arranged in a fully open configuration, and wherein the first portion is detained in contact with the second portion while the device is arranged in the closed configuration.

4. A method for stripping a blockage of material within a medical line, the method comprising:
providing the line stripping device of claim 1;
placing the medical line in the first passage or the second passage;
compressing the medical line between the first and second portions of the line stripping device while the medical line is in the first passage or the second passage; and
while compressing the medical line between the first and second portions of the line stripping device, pulling the line stripping device along the medical line.

5. The method of claim 4, wherein the first passage and the second passage are each tapered passages.

6. The method of claim 5, wherein the tapered passage of the first passage or the second passage, along with the compressing and the pulling, progressively compresses the medical line to move the blockage material within the medical line.

7. The method of claim 4, wherein the medical line is placed in the first passage, and wherein the pulling is performed with the circular opening of the first passage arranged as a leading end of the first passage and the flat slot of the first passage arranged as a trailing end of the first passage in relation to the medical line.

8. The method of claim 4, wherein the medical line in placed in the second passage, and wherein the pulling is performed with the circular opening of the second passage arranged as a leading end of the second passage and the flat slot of the second passage arranged as a trailing end of the second passage in relation to the medical line.

* * * * *

UNITED STATES PATENT AND TRADEMARK OFFICE
CERTIFICATE OF CORRECTION

PATENT NO. : 10,814,111 B2
APPLICATION NO. : 15/729163
DATED : October 27, 2020
INVENTOR(S) : Robert B. Hill and Michael J. Thorn, Jr.

It is certified that error appears in the above-identified patent and that said Letters Patent is hereby corrected as shown below:

In the Claims

In Column 7, Line 4 (Approx.), In Claim 1, after configuration insert -- , --.

In Column 7, Line 15 (Approx.), In Claim 1, delete "slot;" and insert -- slot, --, therefor.

In Column 8, Line 37 (Approx.), In Claim 8, delete "line in" and insert -- line is --, therefor.

Signed and Sealed this
Fifteenth Day of October, 2024

*Katherine Kelly Vidal*
Katherine Kelly Vidal
*Director of the United States Patent and Trademark Office*